United States Patent
Edic et al.

(10) Patent No.: US 9,204,852 B2
(45) Date of Patent: Dec. 8, 2015

(54) SYSTEMS AND METHODS FOR INCREASED ENERGY SEPARATION IN MULTI-ENERGY X-RAY IMAGING

(71) Applicant: General Electric Company, Schenectady, NY (US)

(72) Inventors: Peter Michael Edic, Albany, NY (US); James Walter LeBlanc, Niskayuna, NY (US); Vance Scott Robinson, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 164 days.

(21) Appl. No.: 14/145,445

(22) Filed: Dec. 31, 2013

(65) Prior Publication Data

US 2015/0182179 A1    Jul. 2, 2015

(51) Int. Cl.
*A61B 6/00* (2006.01)
*A61B 6/03* (2006.01)

(52) U.S. Cl.
CPC ............... *A61B 6/482* (2013.01); *A61B 6/035* (2013.01); *A61B 6/4042* (2013.01)

(58) Field of Classification Search
CPC .......... A61B 6/032; A61B 6/035; A61B 6/06; A61B 6/542; A61B 6/482; H01J 35/14; H01J 35/30; G21K 1/02; G21K 1/04; G21K 1/08; G21K 1/087; G21K 1/093; G21K 1/10
USPC .......... 378/16, 98.9, 113, 115, 137, 147, 149, 378/156, 158
See application file for complete search history.

(56) References Cited

U.S. PATENT DOCUMENTS

| | | | |
|---|---|---|---|
| 6,683,934 B1 | 1/2004 | Zhao et al. | |
| 7,649,981 B2* | 1/2010 | Seppi et al. | 378/158 |
| 7,826,587 B1 | 11/2010 | Langan et al. | |
| 8,019,044 B2 | 9/2011 | Shkumat et al. | |
| 8,165,264 B2 | 4/2012 | Zou | |
| 8,265,228 B2 | 9/2012 | Shaw et al. | |
| 8,331,536 B2 | 12/2012 | Shaw et al. | |
| 8,483,361 B2 | 7/2013 | Sainath et al. | |
| 8,494,244 B2 | 7/2013 | Dutta et al. | |
| 8,515,147 B2 | 8/2013 | Baeumer et al. | |
| 2012/0069953 A1 | 3/2012 | Chandra et al. | |
| 2013/0003912 A1 | 1/2013 | De Man et al. | |
| 2013/0101082 A1* | 4/2013 | Jordan et al. | 378/19 |

OTHER PUBLICATIONS

Shkumat et al., "Development and implementation of a high-performance, cardiac-gated dual-energy imaging system", Department of Medical Biophysics, University of Toronto, Toronto, ON, Canada M5G 2M9, pp. 1-12, 2007.

* cited by examiner

*Primary Examiner* — Jurie Yun
(74) *Attorney, Agent, or Firm* — Robert M. McCarthy

(57) ABSTRACT

A filtering device includes an X-ray translucent substrate having a plurality of septa disposed therein at a plurality of fixed positions with respect to the substrate. A controller is programmed to acquire a first set of projection data at a first energy spectrum by controlling the X-ray source to emit the X-rays at the first energy spectrum and controlling the position of the filtering device to focally align the plurality of septa with the X-ray beam emitted from the focal spot, and to acquire a second set of projection data at a second energy spectrum with a mean energy greater than the mean energy of the first energy spectrum by controlling the X-ray source to emit the X-rays at the second energy spectrum and controlling a change in the position of the filtering device to focally misalign the plurality of septa with the X-ray beam emitted from the focal spot.

20 Claims, 8 Drawing Sheets

SYSTEMS AND METHODS FOR INCREASED ENERGY SEPARATION IN MULTI-ENERGY X-RAY IMAGING

BACKGROUND

The subject matter disclosed herein relates to multi-energy X-ray imaging systems and, more particularly, to systems and methods for producing increased energy separation in X-ray spectra applied by such systems.

In modern medicine, medical professionals routinely desire to conduct patient imaging examinations to assess the internal tissue of a patient in a non-invasive manner. For typical single-energy computed tomography (CT) imaging, the resulting X-ray images are largely a representation of the average density of each analyzed voxel based upon the attenuation of X-rays between the X-ray source and the X-ray detector by a patient or object. However, for multi-energy X-ray imaging, a greater amount of imaging data may be gleaned for each voxel. For example, in a dual-energy X-ray imaging system, X-rays with two different spectra are applied to the patient or object; the higher energy X-ray photons are generally attenuated substantially less by patient tissue than the lower energy X-ray photons. In order to reconstruct images from multi-energy CT projection data, the underlying physical effects of X-ray interaction with matter, namely, the Compton scattering effects and photoelectric effects, are incorporated in a process known as basis material decomposition (MD), which is known in the art.

During multi-energy CT data acquisition, a multi-energy X-ray source may be used to apply X-rays having different energy spectra and may be capable of quickly switching from emitting X-rays having one spectrum to emitting X-rays having a different spectrum. Such sources are typically called fast-switching kVp (peak source voltage) sources because the input voltage to the source is switched quickly between high and low potentials to enable acquisition of closely positioned projection data (low-energy projection data and high-energy projection data)—both spatially and temporally. However, the rapid kVp switching requirements from a single X-ray source limits the ability to employ dynamic X-ray beam filtration schemes between the high- and low-energy projection data acquisitions, i.e. rapidly switching a filter out of and into the X-ray beam during low-energy and high-energy acquisitions, respectively. Dynamic filtering schemes are employed to selectively filter the high-energy X-ray spectra to improve the mean energy separation between the low-energy and high-energy spectra. The mean energy of a spectrum is the energy level of an average photon in the spectrum; it is computed by summing all energies in a given X-ray spectrum after weighting each energy by the percentage of photons at that specific energy. Thus, without dynamic filtration, there is significant spectral overlap in the low-energy and high-energy projection data acquisitions—limiting the mean energy separation between the projection data acquisitions. Energy separation is desirable in multi-energy images because it enhances material decomposition methods, which improves the clinical usefulness of the reconstructed images. As known in the art, multi-energy images comprise basis material images, monochromatic images (images reconstructed as if the applied X-ray spectrum consisted of a single energy), or images reconstructed directly from an applied energy spectrum. Accordingly, there exists a need for systems that enable multi-energy X-ray imaging with fast-switching sources that apply energy spectra with improved mean energy separation.

BRIEF DESCRIPTION

In one embodiment, a multi-energy X-ray imaging system includes an X-ray source configured to emit X-rays from a focal spot toward an object to be imaged and an X-ray detector that produces an electrical signal corresponding to the intensity of the X-rays that reach the X-ray detector after being attenuated by the object. A filtering device includes an X-ray translucent support structure having a plurality of septa disposed therein at a plurality of fixed positions with respect to the support structure. The support structure containing the plurality of septa is mounted on a stage that permits it to translate in one or more directions perpendicular to the X-ray beam direction. A controller is programmed to acquire a first set of projection data at a first energy spectrum by controlling the X-ray source to emit the X-rays at the first energy spectrum and controlling the position of the filtering device to focally align the plurality of septa with the X-ray beam emitted from the focal spot. The controller is also programmed to acquire a second set of projection data at a second energy spectrum with a mean energy greater than the first energy spectrum by controlling the X-ray source to emit the X-rays at the second energy spectrum and controlling the position of the filtering device to focally misalign the plurality of septa with the X-ray beam emitted by the focal spot such that the X-rays must pass through and be filtered by the septa.

In another embodiment, a multi-energy X-ray imaging method includes controlling an X-ray source to emit X-rays toward a subject at a first energy spectrum from a focal spot located at a first position and positioning a filtering device in a fixed position with respect to the X-ray source. The filtering device includes an X-ray translucent support structure having a plurality of septa disposed therein at a plurality of fixed positions with respect to the support structure. The support structure is fixed and the septa are focally aligned with the X-ray beam emitted from the focal spot in one of the X-ray focal spot positions. The method also includes acquiring a first set of projection data at the first energy spectrum by detecting the X-rays after passing through the filtering device and the subject. The method further includes deflecting the focal spot to a second position offset from the first position and controlling the X-ray source to emit X-rays toward the subject at a second energy spectrum with a mean energy greater than the first energy spectrum from the focal spot located at the second position and acquiring a second set of projection data at the second energy level by detecting the X-rays after passing through the filtering device and the subject.

In another embodiment, a multi-energy X-ray imaging system includes an X-ray source that emits X-rays from a focal spot toward an object to be imaged and an X-ray detector that produces an electrical signal corresponding to the intensity of the X-rays that reach the X-ray detector after being attenuated by the object. The system also includes a filtering device including an X-ray translucent support structure having a plurality of septa disposed therein at a plurality of fixed positions with respect to the support structure. A controller is programmed to acquire a first set of projection data at a first energy spectrum by controlling the X-ray source to emit the X-rays at the first energy spectrum and controlling the position of the filtering device to focally align the plurality of septa with the X-ray beam emitted by the focal spot. The controller is also programmed to acquire a second set of data at a second energy spectrum with a mean energy greater than the first energy spectrum by controlling the X-ray source to emit the X-rays at the second energy spectrum and controlling a change in the position of the filtering device to focally misalign the plurality of septa with the X-ray beam emitted by the focal spot.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
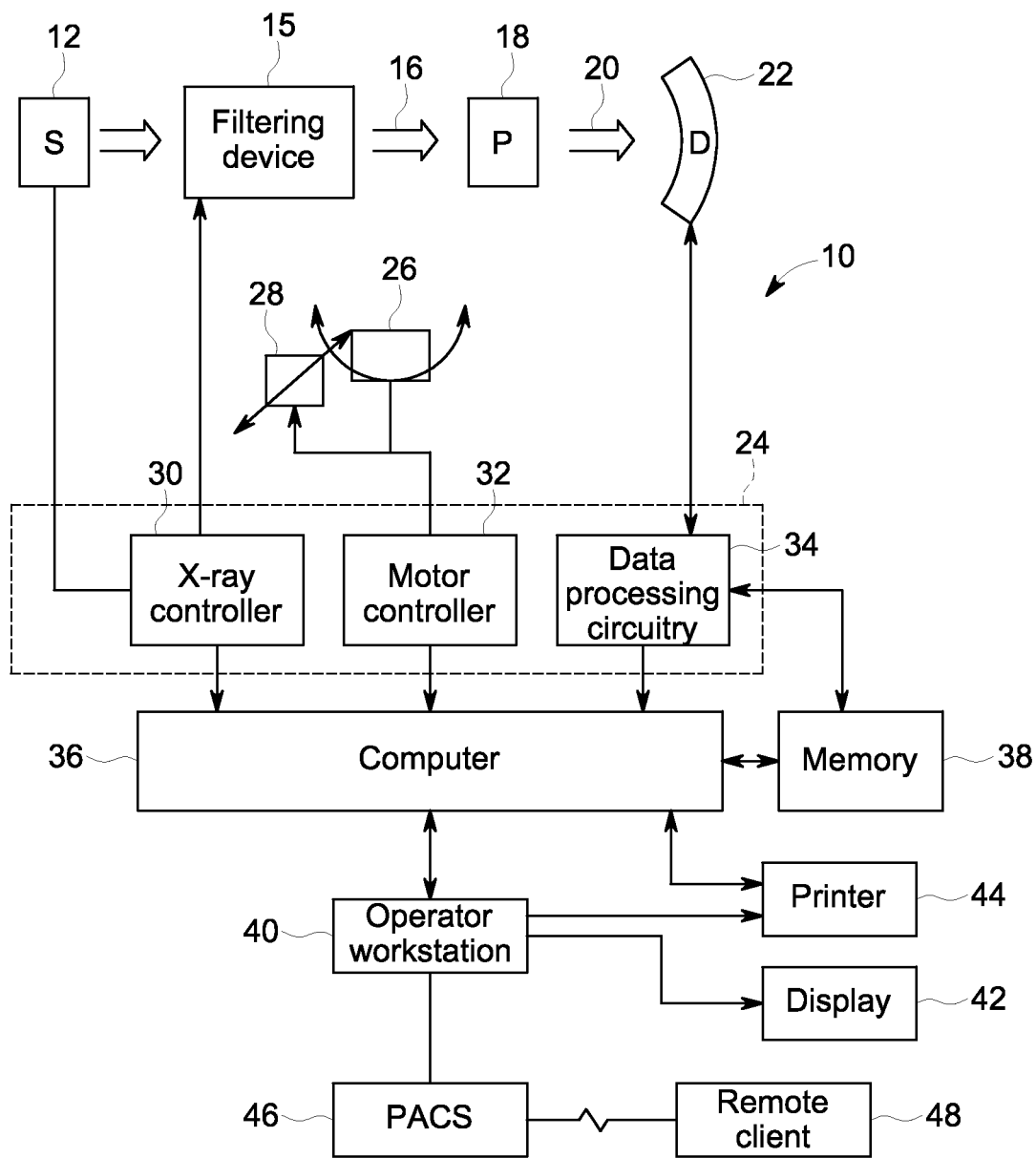
FIG. 1 illustrates an embodiment of a multi-energy CT imaging system, in accordance with aspects of the present disclosure.

The disclosed embodiments are directed to multi-energy X-ray systems and methods that enable increased mean energy separation between applied X-ray energy spectra. For example, one embodiment enables greater mean separation between applied high- and low-energy spectra in dual-energy computed tomography (CT) imaging. In dual-energy CT operations, projection data sets from a patient or object are acquired using two different X-ray energy spectra, e.g. effected from an X-ray tube operating at 80 kVp and 140 kVp, from the single point of reference of the X-ray source and detector relative to the patient or object. Although scanning of a patient will be mentioned hereafter, these techniques equally apply to scanning inanimate objects. By considering the low-energy and high-energy projection data measurements and making assumptions about the materials likely present in the patient's body (i.e., bone, iodine, water, fat, tissue, etc.), different materials within the imaging field of view may be identified. The presently enabled greater mean energy separation in the incident X-ray beam may allow an operator to obtain a resulting image (basis material image or monochromatic image) that provides improved information resulting from multi-energy processing techniques, thereby aiding in clinical diagnosis.

In one embodiment, the increased mean energy separation is achieved by positioning a filtering device, such as a source collimator, between an X-ray source and an imaged subject. The source collimator may include an X-ray translucent support structure and high aspect ratio septa which are focally aligned with the X-ray beam emitted from the focal spot and constructed from material with the appropriate attenuation properties. When acquiring low-energy projection data for dual-energy analysis, the source collimator is adjusted to have a low attenuation profile (positioning to provide minimal attenuation of the X-ray beam), thus minimizing the X-ray intensity reduction due to self absorption. When acquiring high-energy projection data, the position of the source collimator is slightly modified (rotated and/or shifted), thus appropriately shaping the high-energy spectrum by reducing the presence of low-energy photons. Using these methods, the mean energy separation between the low- and high-energy spectra increases, thereby improving the accuracy of material decomposition processing techniques, such as reducing associated noise amplification in the multi-energy processing techniques.

Further, in another embodiment, the source collimator may remain in a fixed position with respect to the X-ray source, and the focal spot of the X-ray source may be repositioned to provide focal misalignment of the X-ray beam relative to the septa in the filtering device. This focal spot misalignment can be used to cause filtering of the X-ray beam as the X-rays pass through the septa. In certain embodiments, the focal spot of the X-ray source may be repositioned through magnetic and/or electrostatic deflection. For example, the X-ray beam emitted from the X-ray source may be passed through one or more electrostatic or magnetic lenses to move the focal spot and provide focal spot misalignment relative to the septa in the filtering device. These embodiments, as well as others, are described in more detail below.

With the forgoing discussion in mind, FIG. 1 illustrates diagrammatically an imaging system 10 for acquiring and processing projection data. In the illustrated embodiment, system 10 is a multi-energy computed tomography (CT) system designed to acquire multi-energy and non-multi-energy X-ray projection data, to reconstruct the projection data into an image, and to process the image data for display and analysis in accordance with the present techniques. Though the imaging system 10 is discussed in the context of medical imaging, the techniques and configurations discussed herein are applicable in other non-invasive imaging contexts, such as baggage, part, or package screening. In the embodiment illustrated in FIG. 1, multi-energy CT imaging system 10 includes a source 12 of X-ray radiation. As discussed in detail herein, the source 12 of X-ray radiation is a multi-energy X-ray source, such as an X-ray tube, or a distributed source configured to emit X-rays from one or more different locations along a surface. For example, the multi-energy X-ray source 12 may include one or more addressable solid-state emitters. Such solid-state emitters may be configured as arrays of field emitters, including one-dimensional arrays, i.e., lines, and two-dimensional arrays. The multi-energy X-ray source is configured to emit X-rays of two or more energy spectra. For example, a multi-energy source may be capable of emitting X-rays of 2, 3, 4, 5, or more different energy spectra upon application of 2, 3, 4, 5, or more different peak operating voltages (kVp) of the X-ray tube.

The multi-energy X-ray source 12 may be positioned proximate to a filtering device 15. However, in other embodiments, the filtering device 15 may be positioned in any implementation-specific position between the X-ray source 12 and the detector 22. In accordance with presently disclosed embodiments, the relative position between filtering device 15 and the focal spot of the X-ray source 12 may be altered to align and misalign filtering elements of the filtering device with the X-ray beam 16 emitted from the focal spot of the X-ray source 12. During alignment, the filtering of the X-ray beam by the filtering elements may be minimized; conversely, misalignment of filtering elements relative to the X-ray beam 16 may enable filtering of the X-ray beam. In this way, the filtering device 15 may be utilized to filter the X-ray beam 16 during exposure at a first energy spectrum and to not filter the X-ray beam 16 (or to minimally filter the X-ray beam 16) at another energy spectrum.

In some embodiments, an additional collimator (not shown) may be included to shape the beam emitted from the X-ray source 12. Such a device may consist of one or more collimating regions, such as lead or tungsten shutters, for each emission point of the source 12. In these embodiments, the collimator defines the size and shape of the one or more beams of radiation 16 that pass into a region in which a subject, such as a human patient 18, is positioned. A beam of radiation 16 may be generally fan-shaped or cone-shaped, depending on the configuration of the detector array. An attenuated portion of the radiation 20 passes through the subject, which attenuates the X-ray beam, and impacts a detector array, represented generally at reference numeral 22.

The detector 22 is generally formed by a plurality of detector elements, which detect the X-rays that pass through and around a subject of interest. Each detector element produces an electrical signal that represents the intensity of the X-ray beam incident at the position of the element during the time the beam strikes the detector. Typically for CT imaging, signals are acquired at a plurality of angular positions around the subject of interest so that a plurality of radiographic views may be collected. These signals are acquired and processed to reconstruct cross-sectional images of the features within the subject, as described below.

The multi-energy X-ray source 12 is controlled by a system controller 24, which furnishes power, focal spot location, control signals and so forth for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry and associated memory circuitry. The associated memory circuitry may store programs and routines executed by the system controller, configuration parameters, image data, and so forth. In one embodiment, the system controller 24 may be implemented as all or part of a processor-based system such as a general-purpose or application-specific computer system.

In the embodiment illustrated in FIG. 1, system controller 24 may control the movement of the filtering device 15, and a linear positioning subsystem 28 and rotational subsystem 26 via a motor controller 32. In imaging system 10 in which the source 12 and/or the detector 22 may be rotated, the rotational subsystem 26 may rotate the X-ray source 12, the filtering device 15, and/or the detector 22 through one or multiple turns around the patient 18. It should be noted that the rotational subsystem 26 may include a gantry. The linear positioning subsystem 28 enables the patient 18, or more specifically a patient table, to be displaced linearly within the gantry. Thus, the patient table may be linearly moved within the gantry or within the imaging volume defined by the combined source 12 and/or detector 22 configuration to generate images of particular areas of interest within the patient 18. In embodiments having a stationary source 12 and a stationary detector 22, the rotational subsystem 26 may be absent or may include a stage to rotate the object 18. Similarly, in embodiments in which the source 12 and the detector 22 are configured to provide extended or sufficient coverage along the Z-axis, i.e, the axis associated along the height of the patient 18, the linear positioning subsystem 28 may be absent.

In certain embodiments, the X-ray controller may control the X-ray source 12, the filtering device 15, or both to achieve one of focal alignment and misalignment between the X-ray beam 16 emitted from the focal spot of the X-ray source 12 and elements of the filtering device 15. For example, in one embodiment, the filtering device 15 may be rotated or translated relative to the X-ray beam emitted from the X-ray source 12 under the control of X-ray controller 30 to effect focal alignment and misalignment of the filtering device 15 with respect to the X-ray beam 16 emitted from the focal spot of the X-ray source 12. Further, in other embodiments, the X-ray controller 30 may control the deflection of the focal spot of the X-ray source to effect one of focal alignment and misalignment between the X-ray beam 16 emitted from the focal spot of the X-ray source 12 and elements of a stationary filtering device 15.

Further, the system controller 24 may include data processing circuitry 34. In this embodiment, the detector 22 is coupled to the system controller 24, and more particularly to the data processing circuitry 34. The data processing circuitry 34 receives data collected by the detector 22. The data processing circuitry 34 typically receives sampled analog signals from the detector 22 and converts the data to digital signals for subsequent processing by a processor-based system, such as a computer 36. Alternatively, in other embodiments, the detector 22 may include a digital-to-analog converter to convert the sampled analog signals to digital signals prior to transmission to the data processing circuitry 34. Additionally, in certain embodiments, the data processing circuitry 34 may be selectively activated by the system controller 24 (e.g., via activation signals) to receive signals from the detector 22.

Additionally, the multi-energy X-ray source 12 and/or the filtering device 15 may be controlled by an X-ray controller 30 disposed within the system controller 24. The X-ray controller 30 may be configured to provide power and timing signals to the X-ray source 12 and/or the filtering device 15. For example, the X-ray controller 30 may include a fast-switching power supply configured to operate the source 12 for at least two or more peak operating voltage levels (kVp) to produce X-rays of two or more energy spectra. The X-ray controller 30 may coordinate the switching of the power supply with the physical repositioning of the filtering device 15 in embodiments that include movement of the filtering device 15. Additionally, in some embodiments, the X-ray controller 30 may include sensing and processing circuitry configured to monitor the position of the filtering device 15.

In certain embodiments, the system controller 24 may include a clock signal (e.g., a processing unit providing a synchronous signal) such that the activities of the components of the CT imaging system 10 may be synchronized. For example, the clock signal may provide signals to enable the system controller 24 to correlate in time the application of a lower or higher peak operating voltage level to the source 12 with the one or more of movement of the filtering device 15 and deflection of the focal spot between a focally-aligned position and a focally-misaligned position of the septa within the filtering device 15 relative to the X-ray beam 16 emitted from the focal spot of the X-ray source 12.

In the depicted embodiment, the computer 36 is coupled to the system controller 24. The data collected by the data processing circuitry 34 may be transmitted to the computer 36 for subsequent processing and reconstruction. The computer 36 may include or communicate with a memory 38 that can store data processed by the computer 36, data to be processed by the computer 36, or routines to be executed by the computer 36, such as for processing image data in accordance with the present technique. It should be understood that any type of computer accessible memory device capable of storing the desired amount of data and/or code may be utilized by such a system 10. Moreover, the memory 38 may comprise one or more memory devices, such as magnetic or optical devices, of similar or different types, which may be local and/or remote to the system 10. The memory 38 may store data, processing parameters, and/or computer programs having one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe the reconstructed image and other data relevant to the system from computer 36, initiate imaging, select and apply image filters, and so forth. Further, the operator may manually identify features and regions of interest from the reconstructed image or the operator may review features and regions of interest automatically identified and/or enhanced through computer-aided geometry determination as discussed herein. Alternatively, automated detection algorithms may be applied to such enhanced features or regions of interest.

A display 42 coupled to the operator workstation 40 may be utilized to observe the reconstructed image. Additionally, the reconstructed image may be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

One or more operator workstations 40 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
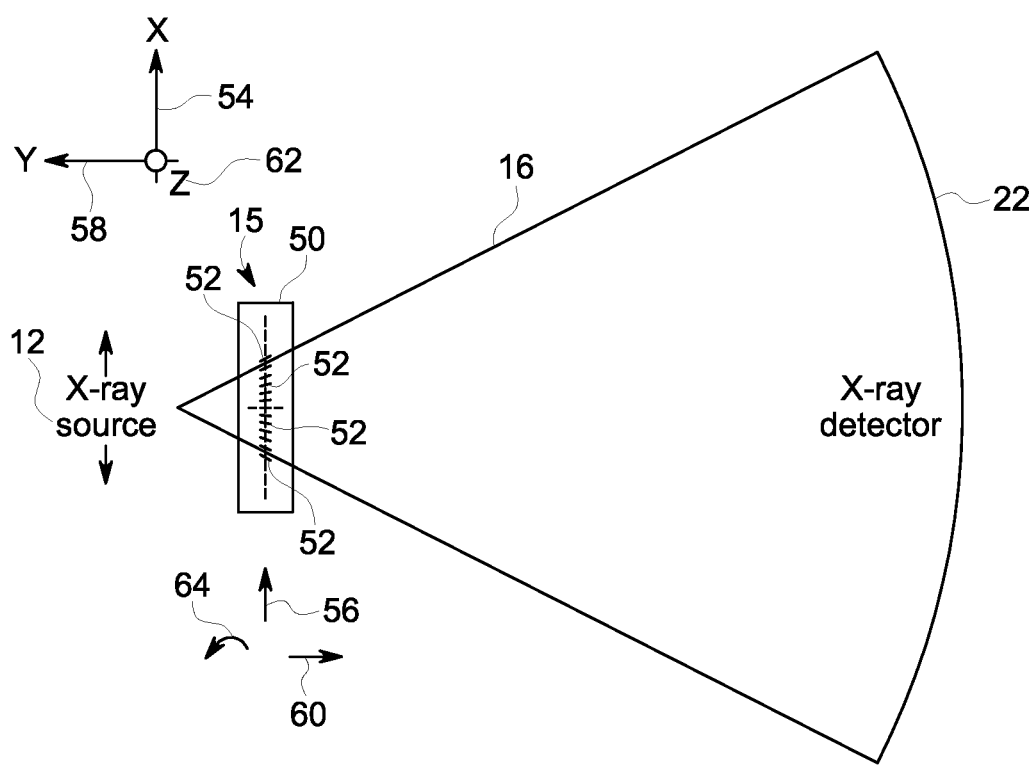
FIG. 2 is a schematic illustrating an X-ray source, an X-ray detector, and a filtering device in accordance with an embodiment.

FIG. 2 is a schematic illustrating a possible placement, structure, and use of the filtering device 15. In this embodiment, the filtering device 15 includes a support structure 50 having a plurality of septa 52 disposed therein. The support structure may be X-ray translucent or of low absorption such that the X-ray beam 16 is not attenuated, or is minimally attenuated, when it passes through the support structure 50. For example, the support structure 50 may be formed from plastic, beryllium, diamond, Si, SiO2, aluminum, Al2O3, boron, graphite, or any other material that minimally attenuates X rays. In such embodiments, the support structure 50 and the plurality of septa 52 may be formed as an integral unit or single device. That is, in some embodiments, the plurality of septa 52 may remain in a fixed position with respect to the support structure 50 during operation because the septa are embedded therein during manufacturing or assembly. For example, in one embodiment, the filtering device may be fabricated by cutting slits into a low absorption support structure (e.g., graphite) and filling the slits with a material having the desired attenuation characteristics. Once filled, the slits form the fixed plurality of septa within the support structure, for example, as described in U.S. Pat. No. 8,265,228, entitled "Anti-Scatter X-Ray Grid Device and Method of Making Same", filed Jun. 28, 2010, and in U.S. Pat. No. 8,331,536, entitled Apparatus for Reducing Scattered X-Ray Detection and Method of Same, filed Sep. 18, 2009, both of which are incorporated by reference in their entirety for all purposes.

In certain embodiments, one or more features of the septa and/or the arrangement of the septa with respect to one another in the support structure may be chosen to facilitate the filtering and non-filtering of the X-ray beam during the high- and low-energy exposures, respectively. For example, the septa may be provided with a high aspect ratio (i.e., ratio of length to width), and the spacing and thickness of the septa may be chosen to minimize X-ray intensity reduction in the "open" or focally-aligned position. That is, in a configuration providing a low attenuation profile ("open" position), the septa 52 are focally aligned with X-ray beam 16 emitted from the focal spot of the X-ray source 12. Since the septa are focally aligned and assumed independent of Z-axis of the imaging system (longitudinal axis of the system), one or more of translation along the X-axis 54, as indicated by arrow 56, translation along the Y-axis 58, as indicated by arrow 60, or rotation about an axis parallel to the Z-axis 62, as indicated by arrow 64, will provide a slight focal misalignment of the septa 52 of the filtering device 15 relative to the X-ray beam 16 emitted from the focal spot of the X-ray source 12. The misalignment between X-ray beam generated from the focal spot of the X-ray source 12 and the plurality of septa 52 can be used to cause filtering of the X-ray beam when the septa are in a "closed" or focally misaligned position.

The aspect ratio of the septa may be chosen to be high and the translation distance or rotation angle may be very small, so that and the translation or rotation necessary to achieve focal misalignment can be accomplished in a time that will meet the switching time requirement of approximately 10-20 microseconds, as dictated by the switching of the X-ray source 12 between subsequent application of the high- and low-energy spectra in a dual-energy configuration. Moreover, the length of the individual septa may be selectively chosen such that at least one of translation (in one or more of the X-axis and Y-axis directions) and rotation of the filtering device causes uniform filtration (or a close approximation thereof) across the complete fan angle of the X-ray beam 16.

Additionally, in some embodiments, the septa may be aligned with a detector collimator to mitigate a further reduction in detective quantum efficiency (DQE) of the detector due to the source filtering device 50, as the "shadow" of the filtering device 15 may fall within the "shadow" of a detector collimator on the detector 22. The detector collimator is used to reduce scattered radiation with the object or patient 18 from striking detector 22. A further advantage of certain embodiments disclosed herein is that the source filtering device 15 may improve the dose efficiency of the CT system when the source filtering device 15 is configured in the "open" position and aligned with the detector collimator, as the filtering device 15 absorbs a percentage of the primary X-rays that would normally strike the detector collimator. Since these X-rays normally traverse the patient 18, but are not absorbed in the detector 22 due to the detector collimator, they contribute to wasted radiation dose.

Further, it should be noted that although the filtering device 15 is illustrated as a single support structure 50 having the plurality of septa 52 disposed therein in FIG. 2, the filtering device 15 may take on a variety of other forms in other embodiments, subject to implementation-specific considerations. For example, in an alternate configuration, the source filtering device 15 may be composed of several discrete sections of incremental filtering devices (e.g. multiple sections of septa 52 have reduced length in a direction parallel to the X-ray beam 16 emitted from the focal spot of the X-ray source 12). When the source filtering device 15 is configured in the "open" position, the incremental filtering devices are positioned such that they are focally-aligned with the X-ray beam 16 emitted from the focal spot of the X-ray source 12 to minimize the attenuation profile, similar to the above-described embodiments. When the source filtering device 15 is configured in the "closed" position, displacement of each section of the incremental filtering devices may be selected such that uniform filtration (or a close approximation thereof) of the X-ray beam 16 across the entire fan angle of the CT system is accomplished. In some embodiments, the discrete sections of the filtering device 15 contain less mass, which will facilitate repositioning of the devices in a time commensurate with subsequent application of the low-energy and high-energy spectra in a dual-energy imaging system.

Additionally, it should be noted that although the filtering device 15 is arranged along the X-axis 54 in FIG. 2, arrangement of the filtering device 15 is not limited to this configuration. For example, in another embodiment, the filtering device 15 may be arranged along the Z-axis.

Figure 3:
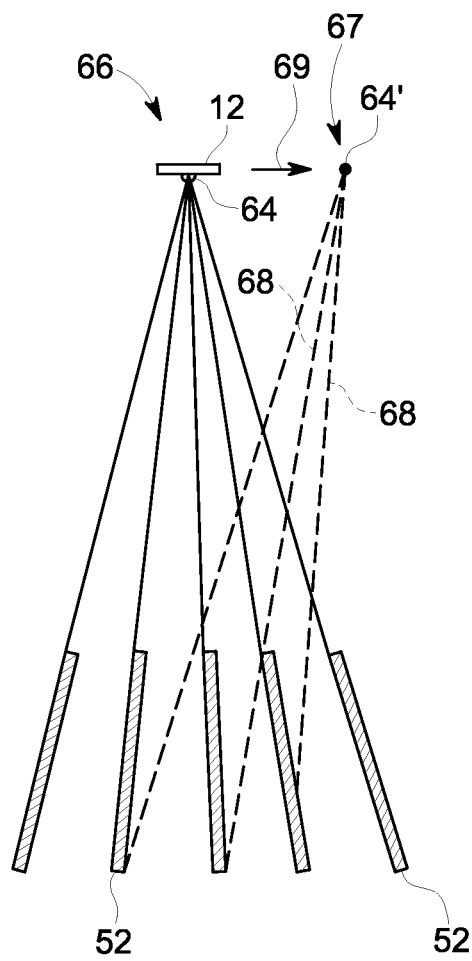
FIG. 3 is a schematic illustrating positioning of the focal spot with respect to a filtering device of an X-ray source in accordance with an embodiment.

FIG. 3 is a schematic illustrating operation in accordance with an embodiment in which the septa 52 remain stationary during the switching time between application of the low-energy and high-energy spectra, but the focal spot is moved to effect the misalignment between the X-ray beam emitted from the focal spot and the septa during application of the high-energy spectrum. As shown, during acquisition of the low-energy projection data, the septa 52 are focally aligned with the X-ray beam emitted from the focal spot 64 in a first position 66. That is, the septa 52 are in a minimal attenuation position so as to minimize filtering of the X-ray beam during application of the low-energy spectrum.

However, during acquisition of the high-energy projection data, the focal spot 64 is moved to the second position 67 along arrow 69 to focal spot 64' by passing the electron beam through one or more electrostatic or magnetic lenses to deflect the focal spot 64 to a new position denoted by the new focal spot 64'. For example, the electron beam may be passed through one or more lenses located in the X-ray source 12. Once the focal spot is deflected to 64', the septa 52, which remained stationary, become focally misaligned with the X-ray beam emitted from the new focal spot 64'. In this way, when the X-rays are directed toward the septa 52 from the new focal spot 64', the X-rays will pass through the septa 52, as indicated by lines 68, thus filtering the X-ray beam for the high-energy spectrum.

Figure 4:
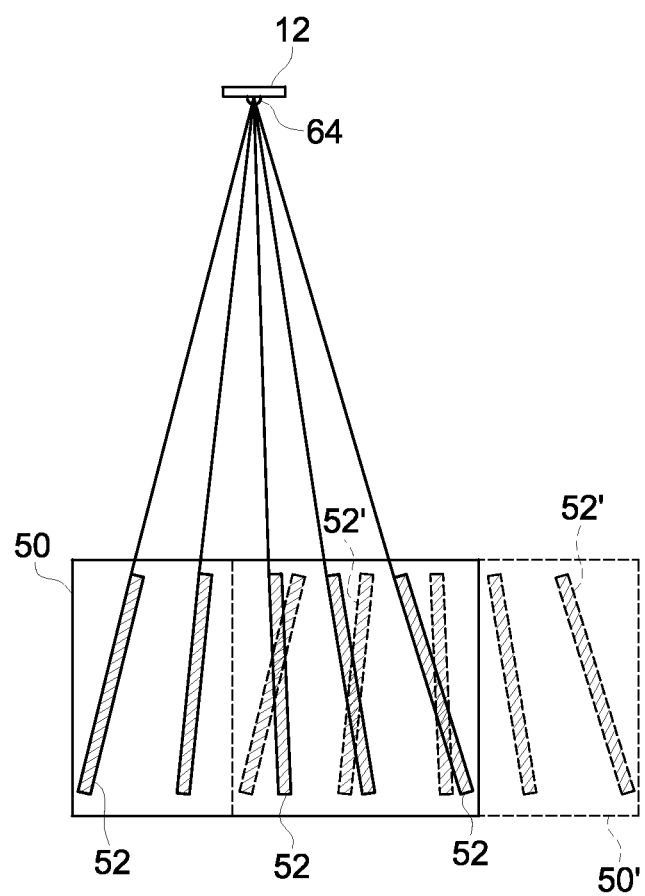
FIG. 4 is a schematic illustrating translation of a filtering device in accordance with an embodiment.
Figure 5:
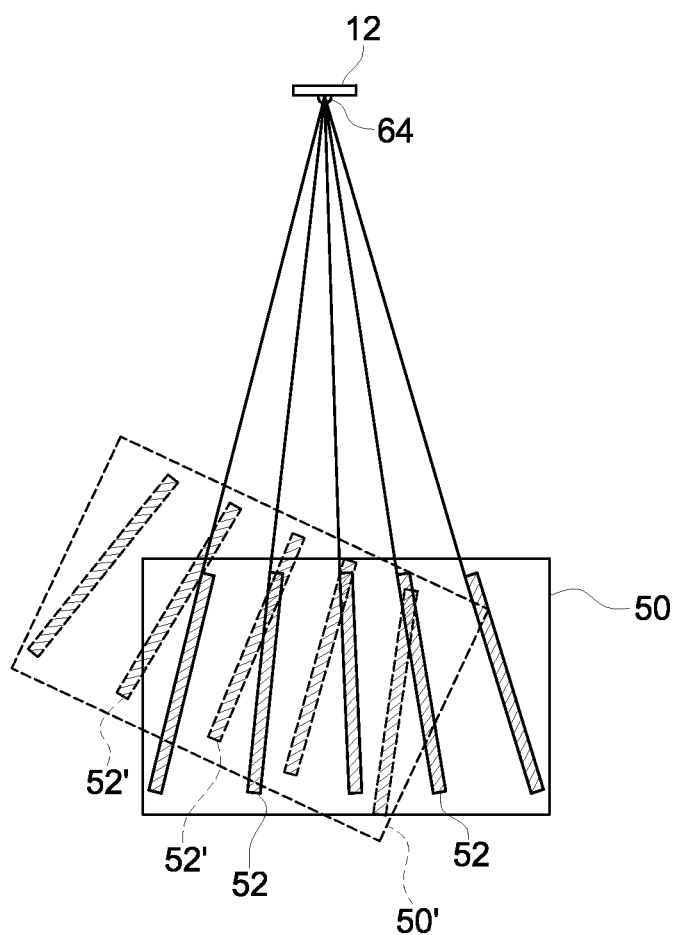
FIG. 5 is a schematic illustrating rotation of a collimator in accordance with an embodiment.

A similar type of filtering may be achieved by one or more of translation and rotation of the filtering device 15, as shown in FIGS. 4 and 5. For example, in FIG. 4, the focal spot 64 remains fixed while the support structure 50 having the septa 52 disposed therein is translated to position 50' having septa 52' still disposed therein. This translation may be along the X-axis or the Y-axis, as shown in FIG. 2. The translation of the filtering device 15 enables the focal spot 64 to remain fixed while achieving misalignment of the X-ray beam emitted from the focal spot of the X-ray source 12 and, thus, filtering, during application of the high-energy spectrum. The translation shown in FIG. 4 is exaggerated for illustrative purposes. Similarly, in FIG. 5, the support structure 50 and septa 52 are rotated about an axis parallel to the Z-axis of the imaging system to their relative new positions 50' and 52' to achieve misalignment between the X-ray beam emitted from focal spot 64 of the X-ray source 12 and the septa 52 during application of the high-energy spectrum. The rotation shown in FIG. 5 is exaggerated for illustrative purposes.

Figure 6:
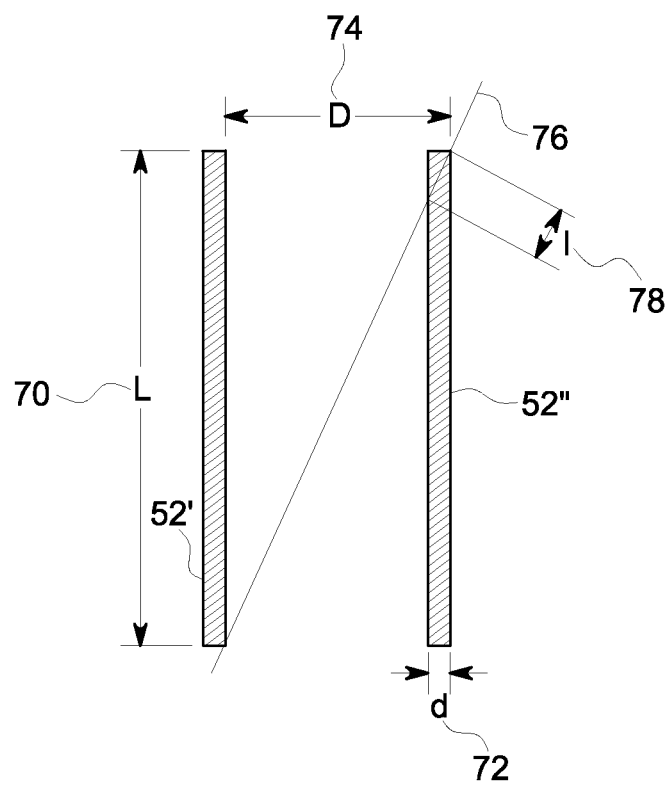
FIG. 6 is a schematic illustrating features of a septa in accordance with an embodiment.

FIG. 6 is a schematic illustrating an embodiment of a first septa 52' adjacent to a second septa 52". In embodiments in which the focal spot 64 is shifted to achieve focal spot misalignment between the septa 52 and the X-ray beam emitted from focal spot 64, it may be desirable to determine certain parameters of the septa 52' and 52" and their relation to one another such that each X-ray passes through only one septa during focal spot misalignment. That is, it may be desirable for each septa 52 to filter the associated portion of the X-ray beam only once during application of the high-energy spectrum.

In the schematic of FIG. 6, the length (L) 70 of the septa 52' is equal to the length of the septa 52", and the width of the septa 52" is defined by distance (d) 72. The inner walls of each of the septa 52' and 52" are separated by a distance (D) 74. An X-ray 76 is shown originating from a shifted focal spot. The effective thickness (l) 78 of the septa 52" for purposes of X-ray filtration is approximately given by the following equation:

$$l \approx d*(L/D). \tag{1}$$

The foregoing parameters may be adjusted to achieve the implementation-specific desired filtering thickness and to ensure that each X-ray in the X-ray beam 16 passes through only one septa. Further, although only two septa are shown in the illustrated schematic, equation (1) may be applied to each pair of adjacent septa.

Figure 7:
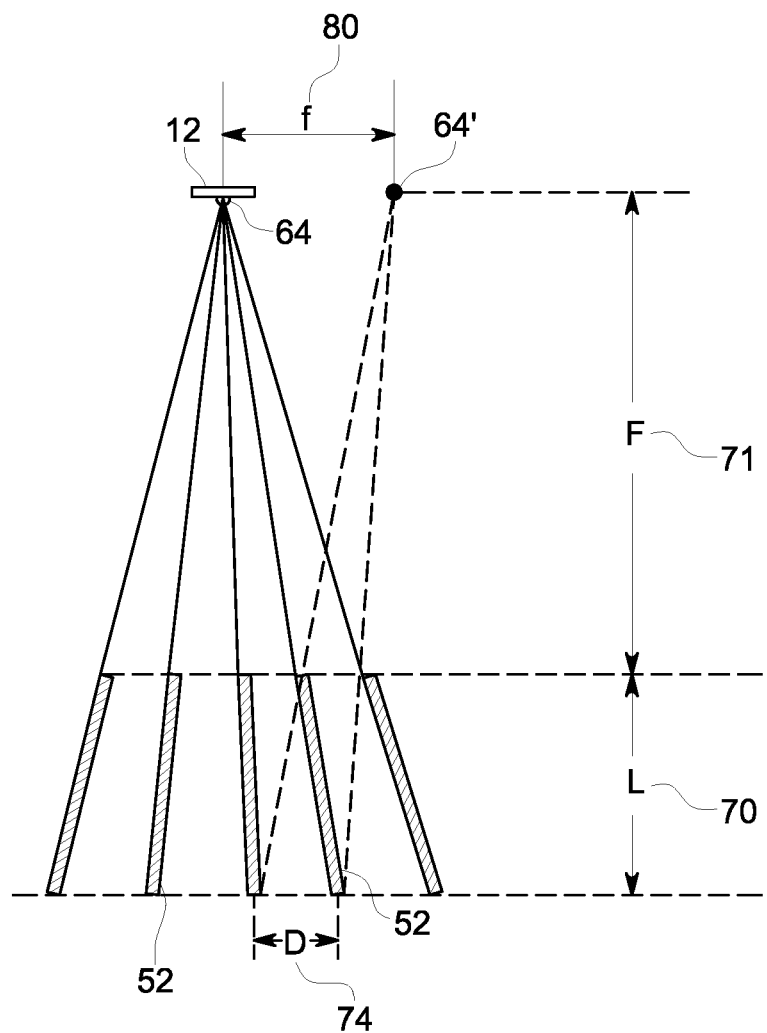
FIG. 7 is schematic illustrating dimensions of an example X-ray acquisition setup in accordance with an embodiment.

FIG. 7 is a schematic further illustrating a way to calculate the focal spot shift distance (f) appropriate for a given embodiment based on the distance (D) between the central septa 74, the length 70 of the central septum (L), and a distance (F) 71 from the focal spot 64 to the septa 52. The focal spot shift distance calculated at the central septum is given by:

$$f = (F*D)/L. \tag{2}$$

Equation (2) may be optimized for any desired implementation to minimize the focal spot shift distance 80. This may be desirable because a reduction in focal spot shift distance 80 may reduce the amount of time required between the low- and high-energy X-ray projection data acquisitions, thereby reducing the overall imaging acquisition time. Further, in other embodiments, it may be desirable to choose the parameters in equation (2) to maximize deflection and achieve improved energy separation with minimal spectral overlap between the high- and low-energy projection data acquisitions. Still further, in some embodiments, it may be desirable to shift the focal spot between the high- and low-energy acquisitions by the width of one septum. Indeed, the parameters of equation (2) may be chosen based on implementation-specific considerations to optimize any desired characteristic.

It should be noted that in the embodiments presented herein, the septa 52 may be formed from any suitable material. For example, the septa 52 may be formed from a high-Z material (e.g., tin, molybdenum, silver, etc.) suitable for filtering the X-ray beam during the high-energy acquisition. Further, the material may be selected such that the material does not have a k-edge located within the energy range associated with the mean energy of the high- and low-energy spectra. For example, the material may be chosen such that it has a k-edge located approximately above the mean energy of the low-energy spectrum (e.g., above 70 keV) or approximately below the average energy of the high-energy spectrum (e.g., below 100 keV). Further, the material may be selected to accommodate constraints imposed by the fabrication process.

Figure 8A:
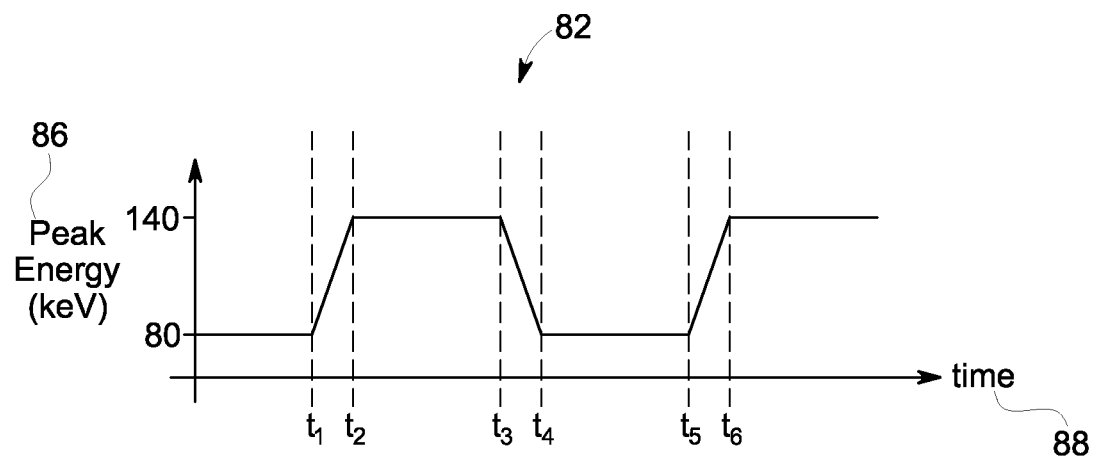
FIG. 8A is a peak energy versus time graph in accordance with an embodiment.
Figure 8B:
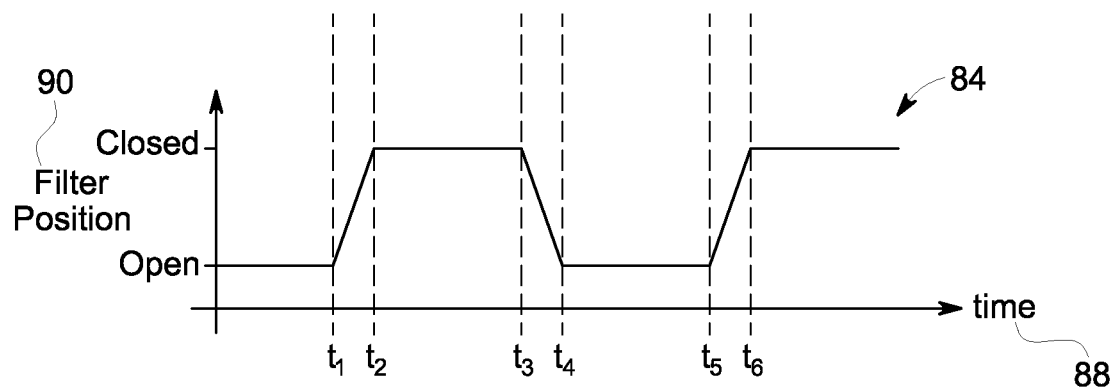
FIG. 8B is a filter position versus time graph in accordance with an embodiment.

FIGS. 8A and 8B illustrate operation of the filtering device 15 and the X-ray source 12 during the acquisition of images with a first and second energy spectra. Specifically, FIG. 8A is a plot 82 of peak energy (keV) 86 versus time 88, and FIG.

8B is a plot 84 illustrating filter position 90 versus time 88. As shown, the filter is in an open position (i.e., a focally aligned position) at $t_1$ when the peak energy of the source is approximately 80 keV. The filter is transitioned to a closed position (i.e., a focally misaligned position) at $t_2$ when the peak energy is transitioned to 140 keV for the high-energy acquisition. Similarly, when the transition from the high-energy spectrum to the low-energy spectrum occurs between $t_3$ and $t_4$, the filter position alternates between the closed position and the open position. This operation is continued throughout the imaging operation, for example, between $t_5$ and $t_6$ during which the filter position again transitions from an open to a closed position.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. For example, although discussed in the context of CT imaging, the techniques described herein are equally useful for multi-energy X-ray imaging systems that provide projection images only of an imaged patient or object.

The invention claimed is:

1. A multi-energy X-ray imaging system, comprising:
   an X-ray source configured to emit X-rays from a focal spot toward an object to be imaged;
   an X-ray detector configured to produce an electrical signal corresponding to the intensity of the X-rays that reach the X-ray detector after being attenuated by the object;
   a filtering device comprising an X-ray translucent support structure having a plurality of septa disposed therein at a plurality of fixed positions with respect to the support structure;
   a controller programmed to acquire a first set of projection data at a first energy spectrum by controlling the X-ray source to emit the X-rays at the first energy spectrum and controlling the position of the filtering device to focally align the plurality of septa with the X-rays emitted from the focal spot, and to acquire a second set of projection data at a second energy spectrum with a mean energy greater than the mean energy of the first energy spectrum by controlling the X-ray source to emit the X-rays at the second energy spectrum and controlling the position of the filtering device to focally misalign the plurality of septa with the X-rays emitted from the focal spot.

2. The multi-energy X-ray imaging system of claim 1, wherein the controller is programmed to focally misalign the plurality of septa with the X-rays emitted by the focal spot by controlling translation of the filtering device along one or more of the X-axis, Y-axis and the Z-axis.

3. The multi-energy X-ray imaging system of claim 1, wherein the controller is programmed to focally misalign the plurality of septa with the X-rays emitted from the focal spot by controlling rotation of the filtering device about an axis parallel to the Z-axis or X-axis.

4. The multi-energy X-ray imaging system of claim 1, wherein one or more electrostatic or magnetic lenses are positioned in the X-ray source for deflecting the focal spot.

5. The multi-energy X-ray imaging system of claim 4, wherein the controller is programmed to focally misalign the plurality of septa with the X-ray beam emitted from the focal spot by controlling the one or more electrostatic or magnetic lenses to deflect the focal spot from a first position to a second position with respect to the filtering device.

6. The multi-energy X-ray imaging system of claim 5, wherein the first position is offset from the second position by a distance greater than or equal to the width of one of the plurality of septa.

7. The multi-energy X-ray imaging system of claim 1, comprising a processor configured to process the first set of projection data and the second set of projection data to compute one or more multi-energy images.

8. The multi-energy X-ray imaging system of claim 1, wherein each of the plurality of septa is made from a material having a k-edge approximately lower than the mean energy of the second energy spectrum or approximately greater than the mean energy of the first energy spectrum.

9. The multi-energy X-ray imaging system of claim 1, wherein each of the plurality of septa comprises copper, tin, molybdenum, silver or a combination thereof.

10. The multi-energy X-ray imaging system of claim 1, wherein the X-ray translucent support structure comprises plastic, beryllium, diamond, Si, $SiO_2$, aluminum, $Al2O3$, boron, graphite or a combination thereof.

11. A multi-energy X-ray imaging method, comprising:
   controlling an X-ray source to emit X-rays toward a subject at a first energy spectrum from a focal spot located at a first position;
   positioning a filtering device in a fixed position with respect to the X-ray source, wherein the filtering device comprises an X-ray translucent support structure having a plurality of septa disposed therein at a plurality of fixed positions with respect to the support structure;
   acquiring a first set of projection data at the first energy spectrum by detecting the X-rays after passing through the filtering device and the subject;
   deflecting the focal spot to a second position offset from the first position;
   controlling the X-ray source to emit X-rays toward the subject at a second energy spectrum with a mean energy greater than the mean energy of the first energy spectrum from the focal spot located at the second position; and
   acquiring a second set of projection data at the second energy spectrum by detecting the X-rays after passing through the filtering device and the subject.

12. The multi-energy X-ray imaging method of claim 11, comprising constructing one or more multi-energy X-ray images from the first set of projection data and the second set of projection data.

13. The multi-energy X-ray imaging method of claim 11, wherein deflecting the focal spot to a second position offset from the first position comprises deflecting the focal spot to the second position offset from the first position by a distance greater than or equal to the width of one of the plurality of septa.

14. The multi-energy X-ray imaging method of claim 11, wherein each of the plurality of septa is made from a material having a k-edge approximately higher than the mean energy level of the first energy spectrum or approximately lower than the mean energy of the second energy spectrum.

15. A multi-energy X-ray imaging system, comprising:
   an X-ray source configured to emit X-rays from a focal spot toward an object to be imaged;
   an X-ray detector configured to produce an electrical signal corresponding to the intensity of the X-rays that reach the X-ray detector after being attenuated by the object;

a filtering device comprising an X-ray translucent support structure having a plurality of septa disposed therein at a plurality of fixed positions with respect to the support structure; and a controller programmed to acquire a first set of projection data at a first energy spectrum by controlling the X-ray source to emit the X-rays at the first energy spectrum and controlling the position of the filtering device to focally align the plurality of septa with the X-ray beam emitted from the focal spot, and to acquire a second set of projection data at a second energy spectrum with a mean energy greater than the mean energy of the first energy spectrum by controlling the X-ray source to emit the X-rays at the second energy spectrum and controlling a change in the position of the filtering device to focally misalign the plurality of septa with the X-ray beam emitted from the focal spot.

16. The multi-energy imaging system of claim 15, wherein the controller is programmed to control the change in the position of the filtering device by controlling a shift in the position of the filtering device along one or more of the X-axis, Y-axis, and Z-axis.

17. The multi-energy system of claim 15, comprising a processor configured to process the first set of projection data and the second set of projection data to construct one or more multi-energy images.

18. The multi-energy system of claim 15, wherein the controller is programmed to control the change in the position of the filtering device by controlling a rotation in the position of the filtering device about an axis parallel to the Z-axis or X-axis.

19. The multi-energy system of claim 15, wherein each of the plurality of septa is made from a material having a k-edge less than the mean energy of the second energy spectrum.

20. The multi-energy system of claim 15, wherein each of the plurality of septa is made from a material having a k-edge greater than the mean energy of the first energy spectrum.

* * * * *